(12) United States Patent
Bledsoe

(10) Patent No.: US 7,166,083 B2
(45) Date of Patent: Jan. 23, 2007

(54) KNEE-ANKLE-FOOT POSITIONING KIT

(75) Inventor: Gary R. Bledsoe, Mansfield, TX (US)

(73) Assignee: Medical Technology, Inc., Grand Prairie, TX (US)

( * ) Notice: Subject to any disclaimer, the term of this patent is extended or adjusted under 35 U.S.C. 154(b) by 309 days.

(21) Appl. No.: 10/737,395

(22) Filed: Dec. 15, 2003

(65) Prior Publication Data

US 2005/0131323 A1     Jun. 16, 2005

(51) Int. Cl.
*A61F 5/00* (2006.01)

(52) U.S. Cl. .......................... 602/23; 602/24; 602/27; 602/62

(58) Field of Classification Search .................. 602/4, 602/5, 12, 23–24, 27–29, 32, 36, 38, 61, 602/62; 128/845, 846, 869, 876, 877, 882, 128/883, 889, 892–894; 2/22; 601/35, 27; 36/1, 84, 99; 482/79, 140; 434/397, 247; 24/578.1
See application file for complete search history.

(56) References Cited

U.S. PATENT DOCUMENTS

| | | | | |
|---|---|---|---|---|
| 1,124,596 A | * | 1/1915 | Dalpe | ........................... 602/29 |
| 3,606,884 A | * | 9/1971 | Peter | ........................... 602/24 |
| 3,730,177 A | | 5/1973 | Thum | |
| 3,759,252 A | | 9/1973 | Berman | |
| 3,815,589 A | | 6/1974 | Bosley | |
| 4,180,254 A | | 12/1979 | Lee et al. | |
| 4,390,015 A | * | 6/1983 | Clements | ..................... 602/23 |
| 4,514,915 A | * | 5/1985 | Galetta | ............................. 36/1 |
| 4,520,805 A | | 6/1985 | St. Vincent et al. | |
| 4,606,334 A | * | 8/1986 | Salmon | ........................ 602/24 |
| 4,620,535 A | * | 11/1986 | Nesbitt | ....................... 128/869 |
| 4,624,060 A | * | 11/1986 | Maxwell | ........................... 36/1 |
| 4,730,609 A | | 3/1988 | McConnell | |
| 4,747,779 A | * | 5/1988 | Gerstung | ..................... 434/247 |
| 4,795,148 A | * | 1/1989 | Rangaswamy | ................ 482/80 |
| 4,815,642 A | * | 3/1989 | Ray | ........................... 224/258 |
| 4,867,359 A | * | 9/1989 | Donovan | .................... 224/602 |
| 5,094,231 A | * | 3/1992 | Rosen | .......................... 602/24 |
| 5,274,933 A | * | 1/1994 | Cole et al. | .................... 36/136 |
| 5,285,939 A | * | 2/1994 | Hogan | ........................ 224/250 |
| 5,286,251 A | | 2/1994 | Thompson et al. | |

(Continued)

FOREIGN PATENT DOCUMENTS

| | | | |
|---|---|---|---|
| WO | WO 97/40805 | * | 6/1997 |

*Primary Examiner*—Henry Bennett
(74) *Attorney, Agent, or Firm*—Locke Liddell & Sapp LLP; Mark R. Backofen

(57) ABSTRACT

A positioning system used to limit movement of the leg, such as when required after hip surgery. In at least one embodiment, a boot, which extends around the foot and lower leg, is secured around each foot. As such, the boots can be used to cushion the feet while applying traction to the leg during surgery. After surgery, the boots are secured together in a side-by-side relationship. In addition, a leg strap is preferably used in conjunction with the boots to help hold the legs together. The leg strap preferably has a cushion that is positioned between the knees with a strap that is secured around each leg. Consequently, the positioning kit restricts certain motion of the affected hip while not restricting movement of the hips and knee and ankle joints unnecessarily.

33 Claims, 3 Drawing Sheets

U.S. PATENT DOCUMENTS

| | | | |
|---|---|---|---|
| 5,289,828 A | 3/1994 | Toth | |
| 5,303,694 A | 4/1994 | Mikhail | |
| 5,476,105 A | 12/1995 | Toth | |
| 5,513,787 A * | 5/1996 | Reed | 224/602 |
| 5,551,950 A * | 9/1996 | Oppen | 601/35 |
| 5,603,336 A * | 2/1997 | Shepich | 128/882 |
| 5,718,672 A * | 2/1998 | Woodman | 602/23 |
| 5,799,654 A * | 9/1998 | Kassan | 128/869 |
| 5,814,001 A * | 9/1998 | Schwenn et al. | 602/24 |
| 5,908,206 A * | 6/1999 | LoPresti, Jr. | 280/814 |
| 5,970,518 A * | 10/1999 | Jordan | |
| 5,971,900 A * | 10/1999 | Miller | 482/140 |
| 6,063,013 A * | 5/2000 | Vathappallil | 482/121 |
| 6,454,335 B1 * | 9/2002 | Wishnick | 294/141 |
| 6,585,672 B1 * | 7/2003 | Crompton | 602/32 |

* cited by examiner

KNEE-ANKLE-FOOT POSITIONING KIT

BACKGROUND OF THE INVENTION

1. Field of the Invention

This invention relates generally to a leg positioning kit and, more particularly, to a leg positioning kit capable of restricting certain movement of the hip following surgery.

2. Description of Related Art

There are a number of issues that result from conducting hip surgery. First, during surgery it is generally necessary to provide traction on the leg in order to hold the bones in the desired position. This traction is often applied by securing the feet to traction plates on a traction table and pulling them away from the hip. As a result of being secured to the traction plates and the traction that is being applied, the feet may be bruised and/or otherwise injured.

Second, during surgery a number of muscles, tendons, and other connective tissue that help maintain the hip in its socket are pulled away or cut in order to provide the surgeon access to the hip joint. After surgery it is important to restrict certain movements of the affected hip in order to promote the healing process of these muscles and connective tissues as well as to prevent dislocation and re-injury of the affected hip. At the same time, it is also undesirable to restrict the movement of the patient's legs more than necessary, in order to help heal and strengthen the muscles surrounding the affected hip joint.

Generally, after surgery the patient is simply placed in a bed and instructed to not move the affected leg in certain directions. Sometimes pillows are also used to help maintain the leg in a desired position. It is often difficult for the patient to prevent undesired movement of the leg, especially while sleeping. In addition, the patient must be frequently rolled into different positions in order to prevent pressure sores from occurring where the patient contacts the bed. This also creates opportunities for the leg to move in an undesirable manner. If the leg is allowed to move in undesired directions, such as rotating, abducting, or adducting, there is a significant chance the hip joint will be dislocated or further injured, thereby prolonging the healing process or even necessitating further treatment or additional surgery.

In some cases, a wedged pillow may be strapped between the patient's legs to restrict motion of the leg. The wider end of the wedge is between the patient's feet and the narrower end between their thighs. By holding the legs against the pillow with straps, abduction and adduction of the hip is restricted. However, this generally does not prevent the rotation of the hip, since only the leg is secured to the pillow with straps, while the foot remains free and allows the leg to rotate. The pillow also unnecessarily prevents the flexion and extension of both the hip and the knee. This prevents the patient from exercising the leg in any way without completely removing the wedged pillow, thereby leaving the leg without any support whatsoever.

Consequently, there is still a need for a simple and inexpensive positioning kit that can restrain the abduction, adduction and rotation of the affected hip while allowing flexion and extension of both the hip and the knee and where the kit can be applied to the patient prior to surgery, both to minimize movement after surgery as well as provide protection for the feet while applying traction during surgery.

SUMMARY OF THE INVENTION

A positioning system used to limit movement of the leg, such as when required after hip surgery. In at least one embodiment, a boot, which extends around the foot and lower leg, is secured around each foot. As such, the boots can be used to cushion the feet while applying traction to the leg during surgery. After surgery, the boots are secured together in a side-by-side relationship. In addition, a leg strap is preferably used in conjunction with the boots to help hold the legs together. The leg strap preferably has a cushion that is positioned between the knees with a strap that is secured around each leg. Consequently, the positioning kit restricts certain motion of the affected hip while not restricting movement of the hips and knee and ankle joints unnecessarily.

BRIEF DESCRIPTION OF THE DRAWINGS

The apparatus of the invention is further described and explained in relation to the following figures wherein.

DETAILED DESCRIPTION OF THE PREFERRED EMBODIMENT

Figure 1:
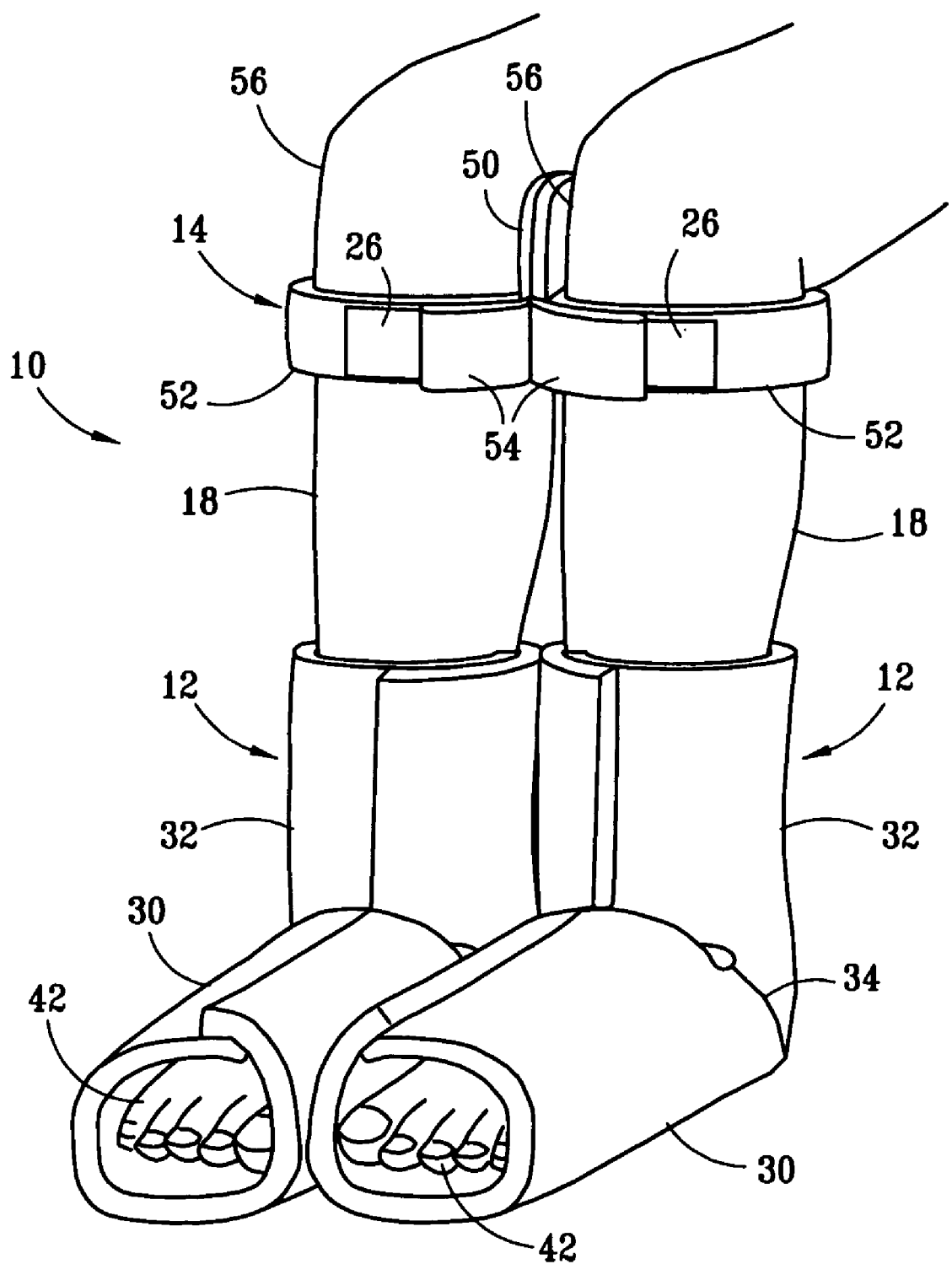
FIG. 1 is a perspective view of a preferred embodiment of the current invention in position on a patient's legs.

In a preferred embodiment, positioning system 10 is generally composed of boots 12 and knee strap 14. Boots 12 and knee strap 14 are preferably composed of thick breathable foam material in order to provide comfort while securely holding legs 18 in the desired position. The surface of boots 12 is composed of many loops that can be used as the loop portion of a hook and loop fastener, such as VELCRO® brand fasteners. These loops can be formed as the integral outer surface of the foam material of boots 12 or it can be a separate material that is secured to the outer surface of the foam in any manner known to those of skill in the art, such as heat fusion or through the use of adhesives. Closure strips 22, 24, and 26 are made up of a plurality of hook segments on one side that make up the other half of a hook and loop fastener system with the loops on the surface of boots 12. Double-sided hook strips 28 are similar to closure strips 22, 24, and 26 except that double-sided hook strips 28 have a plurality of hook segments on both sides to enable it to secure two surfaces together.

Figure 2:
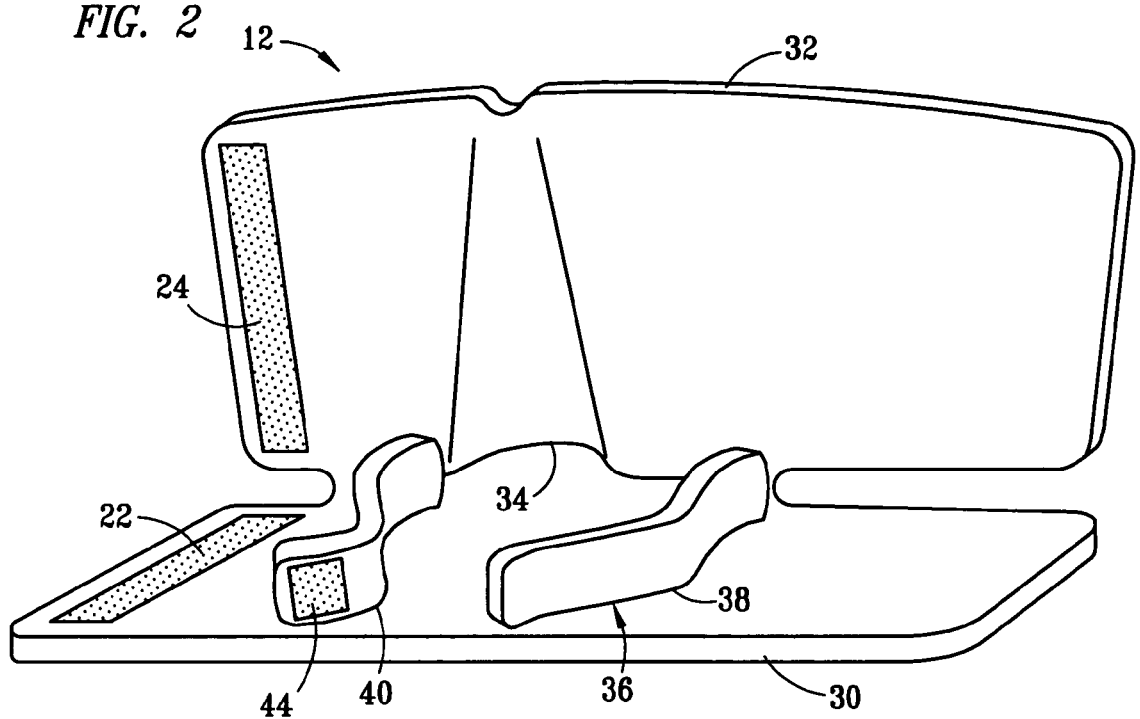
FIG. 2 is a perspective view of one of the boots depicted in FIG. 1 in an open configuration.

With respect to FIG. 2, boots 12 comprise lower wrap 30 and upper wrap 32 secured together at seam 34 as well as ankle strap 36 secured to boot 12 at either end of seam 34. Closure strips 22 and 24 are along one inside edge of boots 12 to securely engage the outer surface of wraps 30 and 32 respectively, thereby securing boot 12 around foot 42 and leg 18. Ankle strap 36 comprises inner strap 38 and outer strap 40 secured to boots 12 at either end of seam 34. Closure strip 44 is disposed at the free end of outer strap 40. While hook and loop closures are preferred, there are many alternate structures and methods, known to those of skill in the art, to secure boot 12 around foot 42, e.g., the use of straps, buckles, zippers, buttons, or other devices, all of which are intended to be encompassed by this invention.

Figure 4:
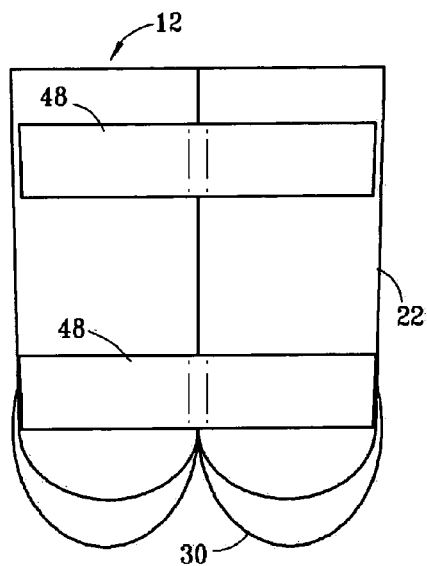
FIG. 4 is a rear elevation view of the boots depicted in FIG. 1.
Figure 5:
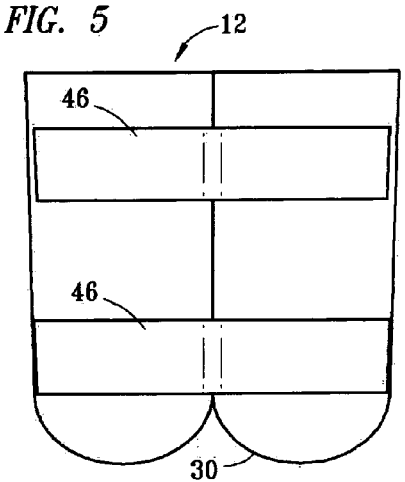
FIG. 5 is a bottom plan view of the boots depicted in FIG. 1.
Figure 6:
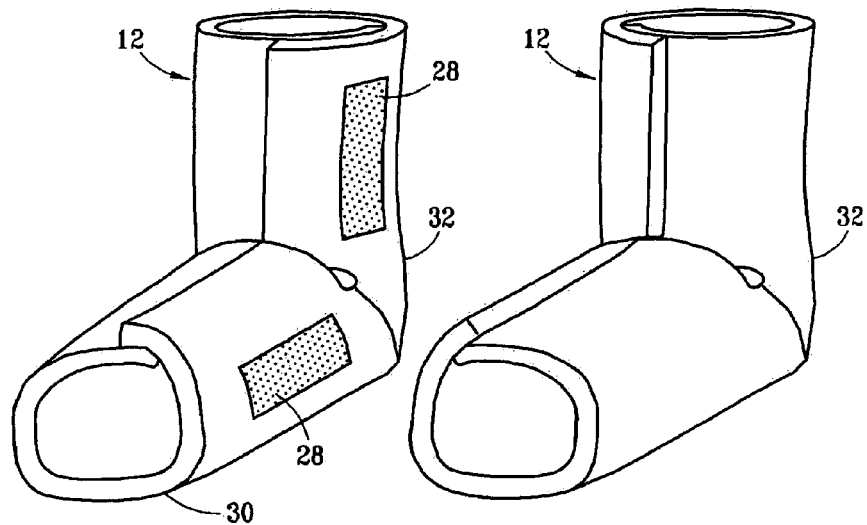
FIG. 6 is a perspective view of the boots depicted in FIG. 1 prior to being secured together.

As shown in FIGS. 4–6, boots 12 are secured together by hook strips 46 and 48 as well as double-sided hook strips 28. As shown in FIG. 6, double-sided hook strips 28 engage the medial side of one boot 12 so when boots 12 are pressed together, the other side of double-sided hook strips 28 engage the medial side of the other boot 12. As shown in FIGS. 4 and 5, lower hook strips 46 and upper hook strips 48 are disposed across boots 12 and engage the outer surface of both boots 12, thereby further securing boots 12 together. One of skill in the art will recognize many alternate structures and methods of securing together boots 12, all of which are encompassed by the current invention. Preferably boots 12 are releasably secured together in order to allow the separation of boots 12 for exercise and physical therapy as the patient heals without the need of removing the entire positioning system 10.

Figure 3:
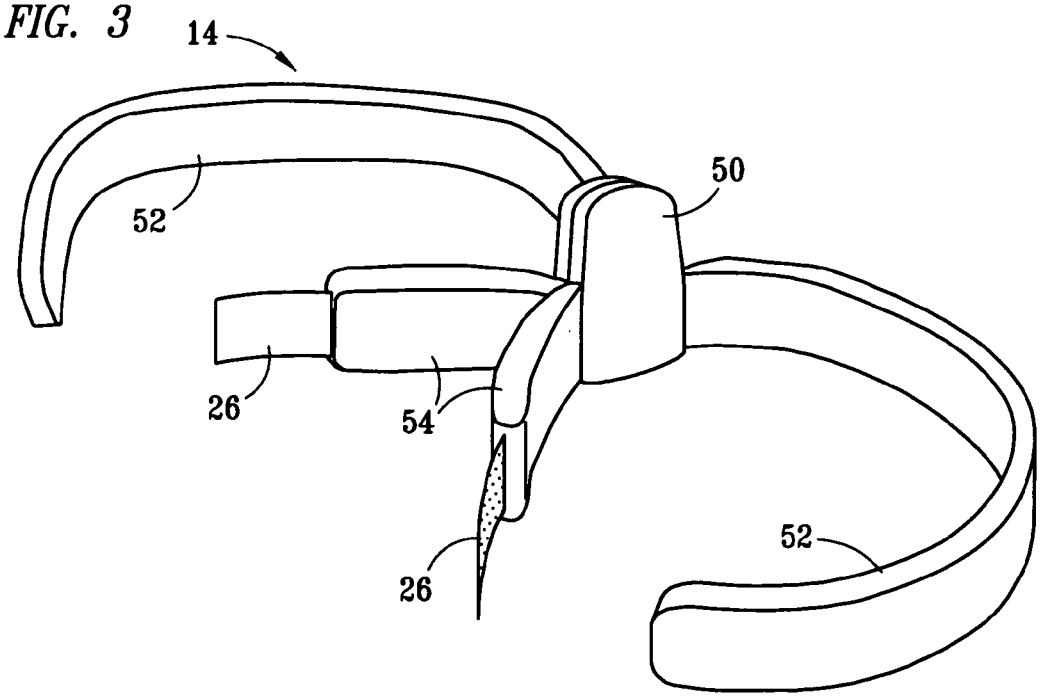
FIG. 3 is a perspective view of the leg straps of the embodiment depicted in FIG. 1 in an open configuration.

As shown in FIG. 3, knee strap 14 is composed of kneepad 50, leg straps 52 and 54, and closure strips 26. Kneepad 50 is disposed between knees 56, as shown with respect to FIG. 1. Kneepad 50 is preferably made of the same breathable foam as boots 12 to cushion knees 56. Leg straps 52 wrap around legs 18, preferably just below knees 56. Leg straps 54 wrap around the other side of leg 18 and contain closure strips 26 that engage the outer surface of leg straps 52.

Positioning system 10 may be used as follows. First, closure strips 22, 24 and 44 on the boot are removed and boots 12 are placed in an open configuration as shown in FIG. 2. Also, hook strips 46, and 48 as well as double-sided hook strips 28 are disengaged from at least one boot 12. Feet 42 are placed in boots 12 with the heel adjacent to seam 34, in the position generally depicted in FIG. 1. Ankle strap 36 is then secured around the top of the patient's ankle by placing inner strap 38 over the ankle and then placing outer strip 40 over inner strap 38 so closure strip 44 engages the outer surface of inner strap 38. Inner strap 38 is preferably shortened by trimming the end so the overlap between straps 38 and 40 is no more than 2–3 inches. Using a long inner strap 38 that can be trimmed, allows positioning kit 10 to be customized to the size of feet 42 and legs 18.

Lower wrap 30 is then placed over the top of the foot 42 and closure strap 22 is secured onto the outer surface of lower wrap 30. Upper wrap 32 is likewise placed over the lower portion of leg 18 and closure strap 24 is secured to the outer surface of upper wrap 32. Wraps 30 and 32 can also be shortened in the same way as inner strap 38 to further customize positioning kit 10. With boots 12 thus secured to feet 42, positioning kit 10 provides cushioning and protection of feet 42 while they are in the foot traction holders of the operative traction table during hip surgery.

At the desired time, either during or immediately following surgery, positioning kit 10 can be used to secure the patient's legs in the desired position. Double sided hook strips 28 are placed on the medial side of one boot 12 so they engage the outer surface of boot 12, as seen in FIG. 6. Boots 12 are then aligned together so that they are at the same level and facing forward and then pressed together so that double-sided hook strips 28 engage the medial side of the other boot 12, thereby securing boots 12 together. Hook strips 46 and 48 are additionally used to further secure boots 12 together. Two lower hook strips 46 are placed across the bottom of boots 12, as seen in FIG. 5, with one approximately across the balls of feet 42 and the other approximately across the heels of feet 42. Two upper hook strips 48 are placed on the back of boots 12, as seen in FIG. 4, with one approximately across the back of the heels of feet 42 and the other higher up across the back of legs 18.

Knee strap 14 is also preferably used to further maintain the legs in the desired position. Kneepad 50 is placed between the patient's knees 56 and positioned with leg straps 52 behind legs 18 and preferably slightly below knees 56. Leg straps 52 are wrapped around the back of legs 18 just below knees 56. While applying tension to straps 52, closure strips located at the ends of leg straps 54 are secured to the outer surface of straps 52. Leg straps 52 can also be shortened by trimming a section at the end to ensure that straps 54 overlap straps 52 by no more than 2–3 inches. In this position, the knees are held together while also being padded for comfort.

Consequently, positioning kit 10 holds the patient's feet 42 and knees 56 together, preventing hip rotation, adduction, and abduction while permitting hip, knee, and some ankle flexion. If it is desired to also limit hip flexion an additional hip brace can be used with positioning kit 10 to accomplish such results. Positioning kit 10 thereby prevents movement of leg 18 that can result in additional damage or a delay in the healing of muscles and connective tissues surrounding the hip that underwent surgery. However, positioning kit 10 also allows some movement of the hip and knee so that the patient can move the leg to some extent, which will aid the healing process. Finally, positioning kit 10, when applied prior to surgery, can help protect feet 42 from bruising and other damage resulting from the necessary application of traction to the leg during surgery.

The above descriptions of certain embodiments are made for the purposes of illustration only and are not intended to be limiting in any manner. Other alterations and modifications of the preferred embodiment will become apparent to those of ordinary skill in the art upon reading this disclosure, and it is intended that the scope of the invention disclosed herein be limited only by the broadest interpretation of the appended claims to which the inventor is legally entitled.

The invention claimed is:

1. A positioning kit for use in limiting movement of a patient's legs comprising:
   two boots, each capable of being secured around a foot and a lower leg of a patient;
   at least one fastening strap capable of securing said boots together; and
   wherein said boots are composed of breathable foam.

2. The positioning kit of claim 1 further comprising a leg strap capable of holding the patient's legs together.

3. The positioning kit of claim 2 wherein said leg strap comprises a cushion and straps capable of holding the patient's legs against said cushion.

4. The positioning kit of claim 2 wherein said leg strap is located adjacent to the patient's knees.

5. The positioning kit of claim 1 wherein each said boot further comprises:
   a lower wrap capable of wrapping around said foot;
   an upper wrap capable of wrapping around said lower leg;
   a seam securing said lower and said upper wraps together; and
   closure strips capable of securing said wraps around said foot and said lower leg.

6. The positioning kit of claim 5 wherein each said boot further comprising an ankle strap capable of wrapping around a patient's ankle.

7. The positioning kit of claim 5 wherein said closure strips are hook fasteners capable of attaching to a pile surface on said boot.

8. The positioning kit of claim 1 wherein said fastening straps comprise hook fasteners capable of attaching to a pile surface on said boots.

9. The positioning kit of claim 1 further comprising double-sided hook fasteners capable of attaching to a pile surface on said boots.

10. A positioning kit for use in limiting movement of a patient's hip comprising:
   two boots, each capable of being secured around a foot and a lower leg of a patient, wherein each said boot comprises a lower wrap capable of wrapping around said foot, an upper wrap capable of wrapping around said lower leg, a seam securing said lower and said upper wraps together, and closure strips capable of securing said wraps around said foot and said lower leg; and
   at least one fastening strap capable of securing said boots together.

11. The positioning kit of claim 10 further comprising a leg strap capable of holding the patient's legs together.

12. The positioning kit of claim 11 wherein said leg strap comprises a cushion and straps capable of holding the patient's legs against said cushion.

13. The positioning kit of claim 12 wherein said leg strap comprises a cushion and straps capable of holding said legs against said cushion.

14. The positioning kit of claim 12 wherein said boots are composed of breathable foam.

15. The positioning kit of claim 12 wherein said boot further comprises:
   a lower wrap capable of wrapping around said foot;
   an upper wrap capable of wrapping around said lower leg;
   a seam securing said lower and said upper wraps together; and
   closure strips capable of securing said wraps around said foot and said lower leg.

16. The positioning kit of claim 15 further comprising an ankle strap capable of wrapping around a patient's ankle.

17. The positioning kit of claim 15 wherein said closure strips comprise hook fasteners capable of attaching to a pile surface on said boot.

18. The positioning kit of claim 17 wherein said fastening straps comprise hook fasteners capable of attaching to said pile surface on said boots.

19. The positioning kit of claim 18 further comprising double-sided hook fasteners capable of attaching to said pile surface on said boots.

20. The positioning kit of claim 11 wherein said leg strap is located adjacent to the patient's knees.

21. The positioning kit of claim 10 wherein said boots are composed of breathable foam.

22. The positioning kit of claim 10 wherein each said boot further comprising an ankle strap capable of wrapping around a patient's ankle.

23. The positioning kit of claim 10 wherein said closure strips are hook fasteners capable of attaching to a pile surface on said boot.

24. The positioning kit of claim 10 wherein said fastening straps comprise hook fasteners capable of attaching to a pile surface on said boots.

25. The positioning kit of claim 10 further comprising double-sided hook fasteners capable of attaching to a pile surface on said boots.

26. A positioning kit for use in limiting movement of a patient's legs comprising:
   two boots, each capable of being secured around a foot and a lower leg of a patient;
   at least one fastening strap capable of securing said boots together; and
   a leg strap capable of holding a patient's legs together.

27. The positioning kit of claim 13 wherein said leg strap is located adjacent to the patient's knees.

28. A positioning kit for use in limiting the movement of a patient's legs comprising:
   two boots, each capable of being secured around a foot and a lower leg of a patient, each said boot comprising, a lower wrap capable of wrapping around said foot, an upper wrap capable of wrapping around said lower leg, a seam securing said lower and said upper wraps together, an ankle strap capable of wrapping around a patient's ankle, and closure strips capable of securing said wraps around said foot and said lower leg;
   wherein said closure strips are hook fasteners capable of attaching to a pile surface on said boot;
   fastening straps capable of securing said boots together, wherein said fastening straps comprise hook fasteners capable of attaching to said pile surface on said boots and double-sided hook fasteners disposed between said boots and capable of attaching to said pile surface on each of said boots;
   a leg strap capable of holding a patient's legs together, said leg strap comprising a cushion between the legs and straps holding the legs against said cushion; and
   wherein said cushion is positioned between a patient's knees.

29. The positioning kit of claim 28 wherein said boots and said leg strap are made of thick breathable foam.

30. The positioning kit of claim 28 wherein said first pile surface is integral with said second pile surface.

31. A method of limiting movement of a patient's legs comprising the steps of:
   securing a boot around at least a portion of a foot and a lower leg of said patient first leg;
   securing a second boot around at least a portion of a foot and a lower leg of said patient's second leg;
   securing said first and said second boots together and
   securing a leg strap around said patient's legs.

32. The method of claim 31 wherein said leg strap is located just below a patient's knees.

33. The method of claim 31 wherein said first and said second boots are secured together by securing fastening straps to each said boot.

* * * * *